United States Patent [19]

Jones et al.

[11] Patent Number: 5,128,005

[45] Date of Patent: Jul. 7, 1992

[54] METHOD FOR SEPARATING IONIC SPECIES USING CAPILLARY ELECTROPHORESIS

[75] Inventors: William R. Jones, Blackstone; Petr Jandik, Framingham; Michael Merion, Upton, all of Mass.; Andrea Weston, N. Providence, R.I.

[73] Assignee: Millipore Corporation, Bedford, Mass.

[21] Appl. No.: 796,757

[22] Filed: Nov. 25, 1991

Related U.S. Application Data

[60] Division of Ser. No. 642,685, Jan. 17, 1991, which is a continuation-in-part of Ser. No. 471,535, Jan. 29, 1990.

[51] Int. Cl.⁵ .................. B01D 57/02; B01D 61/42
[52] U.S. Cl. ................... 204/180.1; 204/299 R; 356/412
[58] Field of Search ........... 204/180.1, 799 R; 356/412; 436/175

[56] References Cited

U.S. PATENT DOCUMENTS 4,414,842 11/1983 Small .................................. 356/412
4,936,974 6/1990 Rose ............................... 204/299 R

OTHER PUBLICATIONS

Foret "Indirect Photometric Detection in Capillary Zone Electrophoresis," J. of Chrom., 470 (1989) pp. 299-308.
Z. Huang et al., Anal. Chem., 61: 766-770 (1989).
F. Foret et al., J. Chromatography, 470: 299-308 (1989).
W. G. Kuhr and E. S. Yeung, Anal. Chem., 60: 2642-2646 (1988).
W. G. Kuhr and E. S. Yeung, Anal. Chem., 60: 1832-1834 (1988).
T. Takeuchi et al., Chromatography, 25: 1072-1074 (1988).
K. D. Atria and C. F. Simpson, Chromatographia, 24: 527-532 (1987).
T. Tsuda et al., J. Chromatography, 264: 385-392 (1983).
J. W. Jorgenson and K. D. Lukacs, Science, 222: 266-272 (1983).
F. Foret et al., Electrophoresis, 7: 430-432 (1986).
Foret et al., Electrophoresis 1990, 11: 780-783 (1990).
Nardi et al., Electrophoresis 1990, 11: 774-776 (1990).

Primary Examiner—John Niebling
Assistant Examiner—Caroline Koestner
Attorney, Agent, or Firm—Hamilton, Brook, Smith & Reynolds

[57] ABSTRACT

A technique for separating, identifying and measuring ions in solution by capillary zone electrophoresis is described, which provides improved sensitivity and resolution of anionic and cationic species. The method involves introducing a sample containing the ionic species into a narrow core capillary filled with a carrier electrolyte containing a selected light-absorbing anion or cation to an electrical current in a capillary column causing the ions to elute according to their ionic mobility. Both UV absorbing and UV-transparent ions can be detected and quantitated by UV/Visible photometric monitoring.

13 Claims, 8 Drawing Sheets

METHOD FOR SEPARATING IONIC SPECIES USING CAPILLARY ELECTROPHORESIS

RELATED APPLICATIONS

This application is a division of application Ser. No. 07/642,685, filed Jan. 17, 1991, which is a continuation-in-part of U.S. patent application Ser. No. 07/471,535, filed Jan. 29, 1990, entitled "Method For Separating Ionic Species Using Capillary Electrophoresis" by William R. Jones, Petr Jandik and Michael Merion.

BACKGROUND

The separation and/or detection of ionic species is generally carried out by utilizing electrochemical properties of analytes, such as ionic interactions and conductivity in ion chromatography or ionic mobility in capillary electrophoresis. Ion chromatography (IC) is capable of detecting simultaneously a large variety of ionic species at low concentration levels. The ability to separate and detect several widely different ionic species simultaneously is a unique characteristic of IC. In fact, the commercial viability of IC depends in part on its ability to simultaneously separate and detect, inter alia, seven common inorganic anions ($F^-$, $Cl^-$, $NO_2^-$, $Br^-$, $NO_3^-$, $HPO_4^-$ and $SO_4^-$). However, there are important limitations to IC, including lack of sufficient selectivity for certain types of mixtures, low separation efficiency and a relative complexity of instrumentation.

Capillary electrophoresis (CE) is an efficient analytical separation technique for analysis of minute amounts of sample. CE separations are performed in a narrow diameter capillary tube, which is filled with an electrically conductive medium termed the "carrier electrolyte". A current is applied to the carrier electrolyte, and ionic species in the sample move from one electrode toward the other at a rate which is dependent upon certain characteristics, such as molecular charge, size and/or mobility. CE may be performed using gels or liquids, such as buffers, in the capillary. In the liquid mode, known as free zone electrophoresis, separations are based on the ratio of charge to Stoke's radius.

CE has several advantages over IC and conventional gel electrophoresis for the separation of ionic species. These include improved resolution and smaller sample size. In part, high resolution can be obtained since band broadening is minimized due to the narrow capillary diameter. In free-zone electrophoresis, the phenomenon of electroosmosis, or electroosmotic flow (EOF), which is the bulk flow of liquid rapidly moves all of the sample molecules whether they are positively charged, negatively charged or neutral. Under certain conditions EOF can contribute to improved separation speed in free-zone CE.

The detection of ionic species by CE is problematical particularly if all seven of the common anions mentioned above are to be determined simultaneously. Most ions do not absorb light, so they cannot be detected by conventional photometric means. e.g., direct photometric or fluorescent detection. However, these ions can be detected using indirect photometric detection. Indirect photometric detection relies upon the presence of a light absorbing electrolyte ion in the background electrolyte. Non-absorbing species are detected as zones of decreased absorbance or voids in the background due to the displacement of the light absorbing electrolyte ion. Indirect photometric detection has been described using fluorescent, ultraviolet (UV) and UV-visible (UV-vis) absorbing ions in the background electrolyte. For example, Small et al. in U.S. Pat. No. 4,414,842 describe a technique for detecting ions in an ion exchange chromatography system by indirect UV detection in which a UV-absorbing ion is included in the elution buffer. Methods utilizing indirect photometric detection in capillary electrophoresis have been described by Foret et al., *J. Chromatography*, 470:299-308 (1989); Kuhr et al., *Anal. Chem.*, 60:2642-2646 (1988); Kuhr et al., *Anal. Chem.*, 60:1832-1834. However, these and other methods have not proved satisfactory. For example none of these methods were able to separate and detect a mixture of eight standard anions ($Br^-$, $Cl^-$, $SO_4^-$, $NO_2$, $NO_3$, $F^-$, $HPO_4^-$ and $CO_3^-$). The main reason is the inability of previously reported indirect photometric methods to provide the same level of sensitivity for UV transparent ions (e.g., $F^-$, $Cl^-$, $SO_4^-$) and UV-absorbing ions (e.g., $NO_2^-$, $NO_3^-$). All published CE methods have failed to successfully separate ions of widely differing properties. e.g., slow migrators such as $F^-$, $PO^-$ and fast migrators such as $Br^-$, $SO_4^-$. The need exists for a method for separating and detecting these and other ionic molecules which is faster, more efficient, has better resolution and requires less sample preparation than the available methods.

SUMMARY OF THE INVENTION

The present invention relates to methods for separating and detecting ions by CE using carrier electrolyte solutions which facilitate detection by indirect methods, particularly UV/visible spectroscopy. The present methods rely upon reagents which can simultaneously effect a sensitive, high resolution separation of several widely different ionic species, ranging from simple inorganic ions to complex organic ions, and both slowly migrating and quickly migrating ions. Methods for separating both anions and cations are disclosed.

The methods generally involve introducing a sample containing the ions into a CE system which utilizes reagents which provide a light-absorbing background at a wavelength suitable for sensitive and interference-free indirect photometric detection of all ionic species without regard to their respective intrinsic UV absorption properties.

The sample is injected into a capillary filled with the carrier electrolyte containing the reagent mixture, an electric current is applied to the capillary under conditions appropriate to cause the ions in the mixture to move toward the oppositely charged electrode and the ionic species are detected photometrically.

The reagent mixture which is most effective as a component in a carrier electrolyte for separating anions consists of the salt of a UV-absorbing anion (e.g., iodide, tungstate, molybdate, chromate, ferrocyanide, ferricyanide or vanadate). Chromate and vanadate compounds are preferred reagents for most anion separations, in part because of their ionic mobilities relative to the common inorganic anions and because of their unusually broad UV spectra. In addition, one or more reagents for controlling the speed and/or direction of the electroosmotic flow of the carrier electrolyte can, optionally, be included in the electrolyte mixture. For example, an alkyl quaternary ammonium, phosphonium or arsonium salt having at least eight carbon atoms in a linear or branched configuration can be added. Sodium chromate is a particularly preferred UV-absorbing salt and tetradecyltrimethylammonium bromide (TTAB) or cetyltrimethylammonium bromide (CTAB) are particularly preferred flow modifiers. Alternatively, the carrier electrolyte can contain only the salt of a UV-absorbing anion while the ammonium, arsonium or phosphonism groups are bound (chemically or by absorptive forces) to the capillary wall.

In addition to the UV-absorbing anion and the flow modifier, an electromigrative agent can be added to the system. The electromigrative agent which enhances the detection of trace anions, e.g., species present in nanomole concentrations and is generally added to the sample containing the analyte ions.

A reagent composition which is an effective carrier electrolyte for separating cations is also the subject of the present invention. The reagent is selected to allow separation and detection of cations having widely different properties (e.g., alkali and alkaline earth cations in a mixture with transition metals). This reagent composition consists of a UV absorbing amine, such as 4-methylbenzylamine, heterocyclic compounds with or without sulfonic groups, such as, for example, 2[N-morpholino] ethanesulfonic acid (MES) or naphthalene sulfonic acid, alkyl or aryl sulfonic acids, with or without additional UV absorbing groups, such as, for example, dodecylsulfonic acid. The carrier electrolyte can, optionally, also contain one or more chelating or complexing agents. The chelating or complexing agents are particularly useful for separating cations having the same or very close mobility.

The chemistry necessary to perform CE separations of ionic species for indirect detection can be contained in a kit. Such a kit for separating anions would contain, inter alia, one or more light absorbing ions specific for the UV/visible range, such as a chromate and/or vanadate salt, and optionally, a quaternary ammonium, arsonium or phosphonium compound. For detecting cations, the kit would contain a UV absorbing cation, such as 4-methylbenzylamine or MES, and optionally, one or more complexing or chelating agents, which are added to the sample in cases where groups of cations having approximately the same mobilities must be separated.

The present reagent compositions and methods have several advantages, such as improved sensitivity, linearity of the range of calibration, the ability to separate and resolve a wide range of anionic and cationic species, the ability to detect ionic species which are not detectable by direct methods in addition to ions that are detectable by direct methods, less sample preparation and faster separation. The methods can be used to separate and detect both simple and complex anions or cations, and to detect a variety of analytes simultaneously.

DETAILED DESCRIPTION OF THE INVENTION

Figure 1:
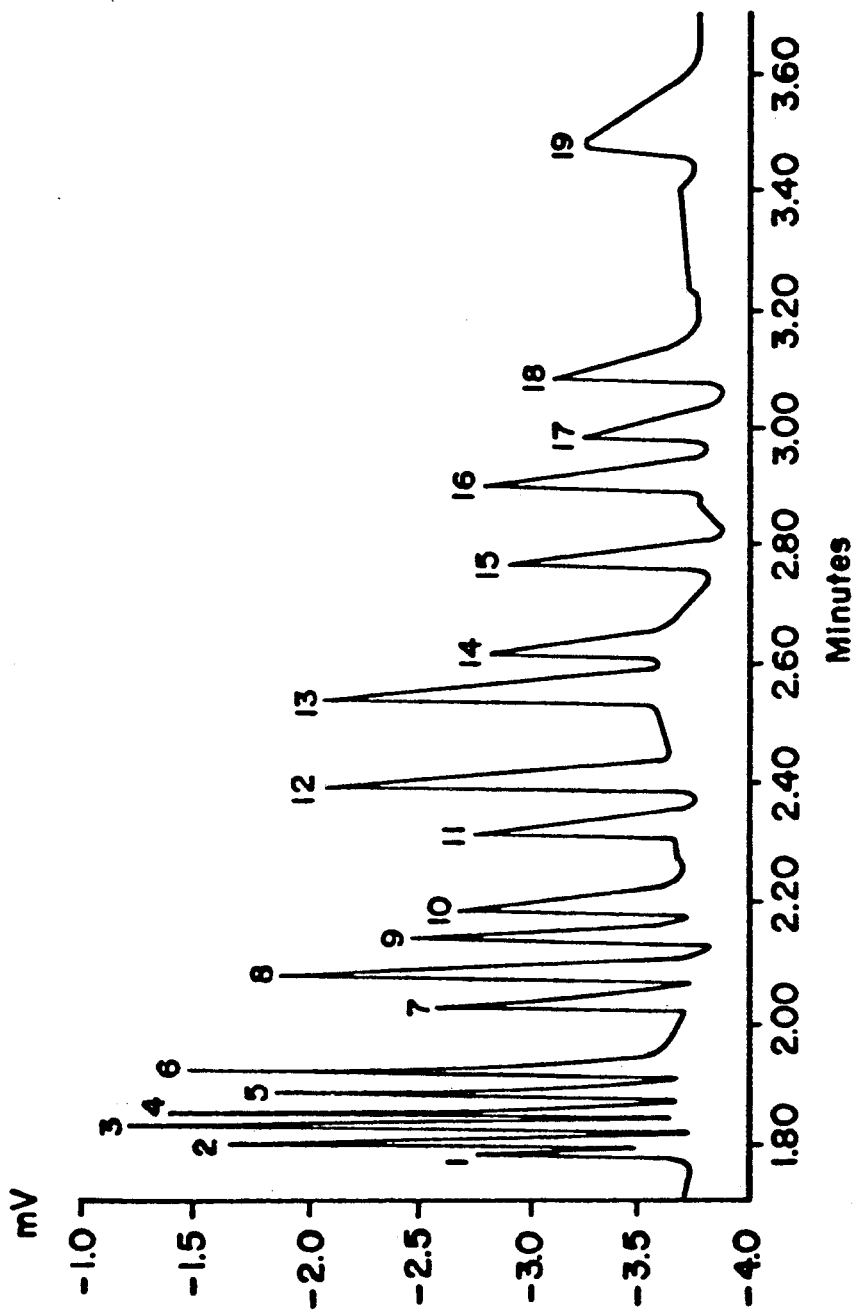
FIG. 1 is a chromatogram showing the separation of nineteen anions by CE using TTAB/$Na_2CrO_4$ as the carrier electrolyte.

The present method utilizes CE to simultaneously separate and detect ionic species having widely different properties contained in a sample using indirect UV/visible detection. Indirect UV/visible spectroscopy is used because many ionic species cannot be detected using direct detection methods. CE is a well known technology, and has been described in detail, for example, by Compton and Brownlee in *Biotechniques*, 6(5):432–440 (1988); and Jorgenson and Lukacs in *Science*, 222:266–272 (1983). A method of utilizing indirect photometric detection in CE is described by Foret et al. in *J. Chromatography*, 470:299–308 (1989).

The present method is generally carried out using the following procedure: a capillary tube is filled with an electrically conductive liquid (the carrier electrolyte) containing one or more reagents which facilitate detection by UV/visible spectroscopy. A preferred capillary is generally a fused silica capillary having an internal diameter of from about 50 to 100 microns ($\mu$).

The ionic sample is introduced into the capillary, for example, by hydrostatic pressure, vacuum or by electromigrative injection in which the liquid sample is moved into the capillary by an electric current. After introduction of the sample, each end of the capillary is immersed in a reservoir which contains an electrode and the carrier electrolyte solution containing the reagents. The capillary tube is positioned with a detector on the column near the end opposite to sample introduction. Electric current is applied causing the anions or cations to move along the capillary toward the opposite electrode. The ions move at different speeds, depending upon several factors, such as their size and mobility. The electrophoretic separation is preferably monitored by indirect UV/visible spectroscopy. Other indirect detection methods can be used, however, UV/visible spectroscopy is preferred because it allows sensitive rapid detection of ionic species and is less costly than laser enhanced fluorescence detection, for example.

The method relies upon reagents which facilitate detection by indirect UV/visible spectroscopy, comprising light-absorbing compounds specific for the UV/visible range. For detecting anions, a UV-absorbing anion is used and for detecting cations, a UV-absorbing cation is used in the carrier electrolyte.

UV/visible light-absorbing compounds which are useful for separating and detecting anions are UV-absorbing anions, such as iodide, tungstate, molybdate, chromate, ferrocyanide, ferrocyanate and vanadate salts. Absorbing anions which are particularly useful are selected chromate and vanadate salts. A preferred chromate salt is sodium chromate ($Na_2CrO_4$) having a concentration of from about 1 mM to about 20 mM. A preferred vanadate salt is sodium vanadate having a concentration of from about 1 mM to about 10 mM.

The carrier electrolyte can also contain, in addition to the UV-absorbing anion, a flow modifier, which is a compound which slows, stops or reverses the electroosmotic flow of the carrier electrolyte. Electroosmotic flow is the bulk flow of the electrolyte through a capillary that is induced by an applied electric field. The amount of flow and its direction is dependent on the charge of the inner wall of the capillary. If there is no wall charge, there is no electroosmotic flow. Thus, flow modifier can eliminate or reverse the effects of the capillary wall on the flow of the electrolyte. Negating or counteracting the wall effects can improve the resolution of the desired analyte ions. Flow modifiers which are useful in the present method include cationic surface active agents, such as alkyl ammonium, arsonium and phosphonium compounds containing at least eight carbon atoms in a linear or branched configuration. Such compounds include for example, quaternary ammonium salts, arsonium salts and phosphonium salts, biammonium salts, biphosphonium salts and biarsonium salts. These compounds include, for example, octyl trimethylammonium, phosphonium or arsonium, various alkyl derivatives of 1,8-diaminooctane, 1,8-diphosphinooctane or 1,8-diarsinooctane. Also suitable are some polymeric ammonium, phosphonium and arsonium salts, such as, for example, hexadimethine bromide. Ampho teric ammonium compounds such as, for example 3(N,N-dimethylpalmityl-ammonio)propanesulfonate are also useful flow modifiers. Compounds which are particularly useful are quaternary ammonium salts which contain alkyl groups having at least eight carbon atoms in a linear or branched configuration. Preferred quaternary ammonium salts are tetradecyltrimethylammonium bromide (TTAB) and/or cetyltrimethylammonium bromide (CTAB). A concentration of TTAB or CTAB of from about 0.1 mM to about 5.0 mM is useful in the present method. The use of flow modifiers facilitates control of both the direction, as well as the rate of electroosmotic flow. Control of this parameter permits the development of an assay that is both high in resolution and is complete in a short period of time. The carrier electrolyte solution generally has a pH of from about 7.5 to about 8.5. An acid, such as sulfuric acid or chromic acid, can be added to the electrolyte solution to adjust the pH to the desired level.

In another embodiment of the present method, various aromatic carboxylic acids can be used as components in carrier electrolytes. The main usefulness of carboxylates as carrier electrolytes is in the CE analysis of less mobile anions (e.g., fluoride, carboxylic acids, alkylsulfonates), which may produce broadly asymmetric peaks if analyzed using the chromate electrolyte. However, because of their relatively low mobilities, aromatic carboxylates are less suitable than chromates as electrolytes for analysis of complex mixtures of highly mobile inorganic anions. The best results are obtained in CE when the mobilities between the main anionic components of the carrier electrolyte and the analyte ions is closely matched. Therefore, a range of highly UV-absorbing carrier electrolytes covering the range of ionic mobilities of all inorganic anions and other low molecular weight species is of practical interest. Aromatic carboxylates are useful in the present method for detecting and measuring some organic anionic species having low ionic mobility and which are UV-transparent, such as carboxylic acids, amino acids, carbohydrates or sulfonates. Aromatic carboxylates such as phthalate, trimesate, benzenetetracarboxylate, p-hydroxybenzoate, and p-anisate are useful for this purpose.

In another embodiment of the present composition and method for separating and detecting anions, an electromigrative agent can be added to the sample in order to enhance the separation and/or detection of trace amounts of anions, e.g. nanomolar quantities. The addition of an electromigrative agent to the sample provides enrichment of the separation of anions present in the sample in concentrations in the nanomolar range. In this embodiment, the agent is added to the sample, and the sample is injected into the capillary using electromigrative sample introduction. Electromigrative sample introduction involves applying a current having very low amperage which selectively causes the trace anions to migrate toward the capillary. The addition to the sample of the electromigrative agent, which has a lower ionic mobility in comparison to the carrier electrolyte anion, results in the selective migration of the trace anions into the capillary, which effectively preconcentrates these anions, thereby enriching the sample to be analyzed with the trace anions. In addition to the analyte anions, it is also possible to observe the enrichment of sample matrix anions acting as an isotachophoretic terminating electrolyte. Such anions may be added purposely. In solutions containing total ionic concentrations in the nanomolar range, sample conductivity often becomes too low, and can be adjusted by a suitable additive to enable sufficient electric charge throughput for ionic transfer from the bulk of the sample solution into the capillary. For this purpose, citrate, carbonate and octanesulfonate salts can be used as electromigration additives.

Figure 5:
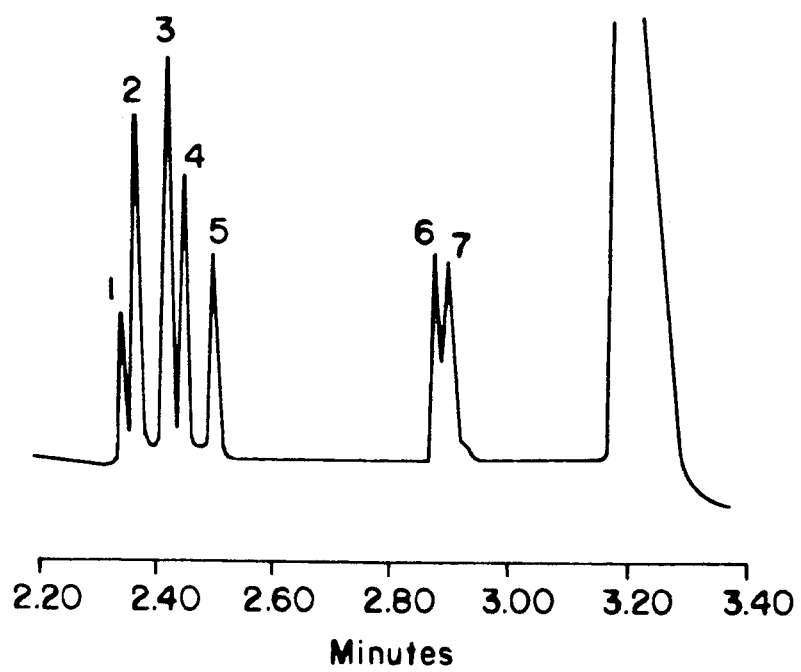
FIG. 5 is a chromatogram showing the separation of eight anions by CE using TTAB/$Na_2CrO_4$ and octanesulfonate as an electromigrative agent.

Citrate, carbonate and octanesulfonate salts which exhibit lower ionic mobilities in comparison with the UV-absorbing anion in the carrier electrolyte (e.g., chromate) can be used as additives for electromigrative trace enrichment with the UV-absorbing anions in the carrier electrolyte. Sodium octanesulfonate adjusted within the range of 15 to 40 $\mu$m is particularly useful electromigration agent in low ionic content samples. Addition of relatively excessive concentrations of octanesulfonate does not lead to interfering comigration with any of over fifty anionic species analyzed by the present CE method. Sodium octanesulfonate can be obtained free of common ionic impurities which could disturb the quantitation of common anions such as sulfate and chloride in unknown samples. An example of a separation of common inorganic anions at low ppb levels using sodium octanesulfonate as an electromigrative agent is shown in FIG. 5. As indicated, the detection limits (calculated as noise times three in concentration units) for this separation are in the low nanomolar range. This represents at least a hundredfold increase in sensitivity in comparison with the results achievable in the same carrier electrolyte and with hydrodynamic sample introduction.

UV/visible light-absorbing compounds which are useful in the present method for separating and detecting cations are UV-absorbing cations, such as 4-methylbenzylamine, 2-aminopyridine, 2-amino-4,6-dimethylpyridine, MES, 3-[(3-cholamidopropyl)dimethylammonio]-1-propane sulfonate (CHAPS) and N-[2-hydroxyethyl]piperazine-N'-[3-propane sulfonic acid]-

(EPPS). 4-Methylbenzylamine is the preferred UV-absorbing cation in the present method. The concentration of 4-methylbenzylamine is generally from about 3 mM to about 10 mM. The reagent mixture for cation separation can optionally contain a complexing or chelating agent, such as ethylenediaminetetraacetic acid (EDTA), citrate, tartrate, hydroxyisobutyrate, oxalate and succinate. The complexing agent allows cations having the same or similar mobilities to be differentiated.

The present methods can be utilized to analyze most types of ionic species. Samples containing complex mixtures of ions, including anions, cations and organic compounds, for example can be analyzed using the method. When a sample containing such a complex mixture is separated using the present methods and electrolyte carriers for separating anions, for example, the detector is placed just before the anode immersed in an electrolyte and the cathode is placed in another portion of the same electrolyte at the opposite end. Thus, the cations in the sample will move away from the detector, and the organic species will move very slowly toward the anode, thereby creating a window for the anionic species toward the detector. The anions move most rapidly toward the detector, thus are most efficiently resolved. Where a method and electrolyte carrier appropriate for separating cations is used, the polarity of the electrodes is reversed, and the cations will move toward the detector (i.e., toward the cathode) while the anions in the sample will move away from the detector.

The present methods are useful for analyzing samples containing multiple ionic species in the shortest time possible, or to scan an unknown sample for ionic compounds, since the methods and reagent mixtures can efficiently separate and resolve such mixtures. Samples which can be analyzed using the present methods include water, foods, such as juices, biological fluids or industrial chemical mixtures.

In one embodiment of the present method, a sample containing eight common inorganic anions: bromide, chloride, nitrate, nitrite, sulfate, fluoride, phosphate and carbonate, was analyzed by CE using a mixture of 0.5 mM TTAB and 5 mM sodium chromate ($Na_2CrO_4$) having a pH of 8 as the carrier electrolyte. All eight anions were detected by monitoring the absorbance of the carrier electrolyte at 254 or 272 nm. Separation of all eight anions was completed in about three minutes. The ionic species were separated based on their ionic mobilities. This is important because the elution sequence using the present method is predictable based on the known ion mobilities of various ions. This means that the chemical identity of an unknown analyte can be reliably determined from its position in the elution order.

In another embodiment of the present method, a sample containing seven inorganic cations: potassium, barium, strontium, sodium, calcium, magnesium and lithium, was analyzed by CE using 5 mM 4-methylbenzylamine in 0.21 mM citrate having a pH of 5.5 as a carrier electrolyte. All seven cations were detected by monitoring the absorbance of the carrier electrolyte at 214 mM. Separation of all seven cations was complete in less than three minutes.

Separation of ionic species using the present compositions and methods is superior to ion chromatographic separations of similar mixtures in several respects: improved separation efficiency, shorter runtime, better selectivity, linearity of the plot and improved sensitivity. For example, the number of theoretical plates for sulfate in the illustrative example used above is 157,344. The highest plate-counts attainable by ion chromatography are smaller than 10,000. Separation of the standard eight anions was completed in three minutes by the present method, whereas ion chromatographic separations of identical mixtures take typically six to fifteen minutes. Injection volumes for the CE separation are less than about 40 nanoliters (nl) compared to about 50 to 100 microliters ($\mu l$) for IC. Even though only 20 nL were injected to obtain the above separation, detection limits for all separated anions were either comparable or better than those observed in IC. This corresponds to a 10,000 fold increase in absolute sensitivity (per $\mu g$ injected) in the present CE system in comparison with IC.

The present methods provide ionic separations which are efficient, highly selective, and which have a predictable order of elution. The methods exhibit increased selectivity for ionic separations as compared to other methods such as IC. During a typical CE separation of anions using the present chromate reagent mixture, cationic compounds migrate in the opposite direction away from the anions of interest and are not seen in the electropherogram. Conversely, during a typical CE separation of cations using the methylbenzylamine reagent mixture, anionic compounds migrate in the opposite direction away from the cations of interest. Neutral and slightly polar impurities are considerably less mobile than the anions or cations and have longer migration times. Thus, the anions or cations of interest are efficiently separated and resolved in the shortest time.

The practical usefulness of such increased selectivity can be illustrated, for example, using a fruit juice as the sample. When orange juice is directly injected into an IC system, the first five peaks to elute, which represent fluoride, chloride, nitrite, bromide and nitrate ions, are subjected to interference by carboxylic acids, such as formate or acetate and other organic compounds in the sample. To reduce this interference, analysis of the anions in the juice using IC would require a complicated pretreatment of the sample to remove the carboxylates and organic compounds. The same sample can be successfully analyzed by CE, and good separation of the anions can be obtained without any pretreatment of the sample using the present method.

The invention is further illustrated by the following Examples.

EXAMPLE 1

General Procedure for CZE of Anions Using $Na_2CrO_4$/TTAB Electrolyte

A sample containing the following eight inorganic anions was prepared: fluoride (F), carbonate ($CO_3$), chloride (Cl), nitrite ($NO_2$), nitrate ($NO_3$), bromide (Br), phosphate ($H_2PO_4$) and sulfate ($SO_2$).

A fused silica capillary externally coated with polyimide (Polymicro Technologies) was freshly cut from a roll and approximately 1 cm section of polyimide coating was burned off with a butane lighter for UV to pass through at 40.5 cm from one end. The total capillary length was 63 cm. and had an internal diameter of 75 $\mu m$. The capillary was installed into the cell and purged with electrolyte with a 1 cc luer syringe with an adapter. The electrolyte was 5 mM $Na_2CrO_4$ and 0.5 mM TTAB, adjusted to pH 8 with 10 mN sulfuric acid. A 50 ml beaker and a 100 ml beaker were filled with electrolyte to equal heights. The 50 ml beaker was placed at the cathode end of the capillary and the 100 ml was placed at the anode end Approximately 100 microliters of carrier electrolyte was run through the capillary prior to analysis.

The power supply (Spellman (0 to 30 KV)) was manually turned to zero. The capillary at the cathode end was picked up manually, raised to 16 cm height above the electrolyte level and placed in the sample for 30 seconds. The capillary was removed from the sample and placed promptly into the electrolyte. The voltage was manually ramped from 0 to 20 KV during approximately 10 seconds while the start integrate signal was initiated at the beginning of the voltage ramp. At 20 KV a typical current reading was about 20 μA.

Detection was carried out using a Linear Instruments variable UV/Vis CE detector at two different wavelengths: 254 nm and 272 nm.

Separation was completed in about three minutes, and a clear and distinct peak was obtained for each anion. All eight anions were separated within about one minute.

EXAMPLE 2

CE Separation of a Complex Mixture of Anions

The separation of a complex mixture of ten (10) weakly and strongly dissociated anionic species was carried out according to the procedure described in Example 1. The ten anions in the mixture were: Cl, $SO_4$, $NO_3$, F, $CO_3$, formate, acetate, propionate, butyrate and an unidentified organic acid. Separation was completed within about 3.8 minutes. All ten anions eluted and were detected, and a clear and distinct peak was obtained for each anion.

EXAMPLE 3

CE Separation of a Complex Mixture of Nineteen Anions

The separation of a complex mixture of nineteen anionic species was carried out according to the general procedure described in Example 1. The injection volume was 20 nl, and indirect UV/visible detection was carried out at 272 nm. The nineteen anions were:

|  | anion | ppm |
| --- | --- | --- |
| 1. | bromide | 4 |
| 2. | chloride | 2 |
| 3. | sulfate | 4 |
| 4. | nitrite | 4 |
| 5. | nitrate | 4 |
| 6. | molybdate | 20 |
| 7. | citrate | 4 |
| 8. | fluoride | 1 |
| 9. | phosphate | 4 |
| 10. | phoshite | 4 |
| 11. | phthalate | 4 |
| 12. | methanesulfonate | 5 |
| 13. | ethane sulfonate | 5 |
| 14. | acetate | 5 |
| 15. | propanesulfonate | 5 |
| 16. | butane sulfonate | 5 |
| 17. | benzoate | 5 |
| 18. | pentane sulfonate | 5 |
| 19. | hexane sulfonate | 5 |

Separation was completed in less than four minutes. All nineteen anions were detected and a clear and distinct peak was obtained for each anion, as shown in FIG. 1. The numbers on the peaks correspond to the numbers in the above list of anions.

EXAMPLE 4

Comparison of a CE Separation and an IC Separation of Fifteen Anions

The separation of a mixture of 15 anions was carried out by CE according to the procedure set out in Example 3. The same mixture was separated by IC according to standard IC conditions. The fifteen anions were:

|  | anion | ppm |
| --- | --- | --- |
| 1. | thiosulfate | 4 |
| 2. | bromide | 2 |
| 3. | chloride | 2 |
| 4. | sulfate | 4 |
| 5. | nitrite | 4 |
| 6. | nitrate | 4 |
| 7. | molybdate | 20 |
| 8. | tungstate | 20 |
| 9. | monofluorophosphate | 4 |
| 10. | citrate | 4 |
| 11. | fluoride | 1 |
| 12. | phosphate | 4 |
| 13. | phosphite | 4 |
| 14. | phthalate | 4 |
| 15. | carbonate | 4 |

Figure 2A:
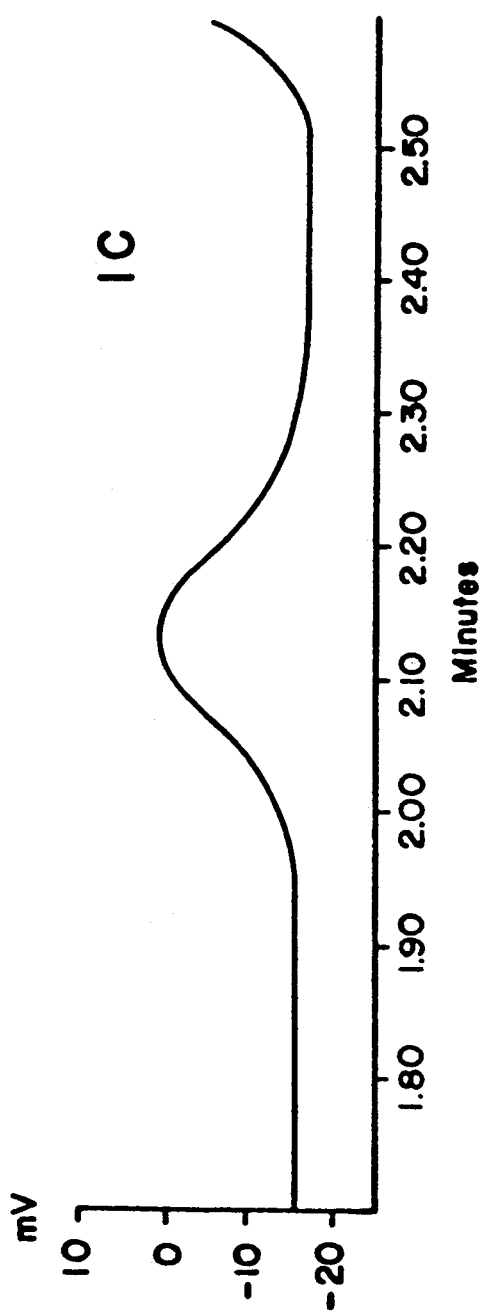
FIG. 2 compares (A) a chromatogram showing the separation of fifteen anions using IC; with (B) a chromatogram showing separation of the same mixture of anions by CE using TTAB/$Na_2CrO_4$ as the carrier electrolyte.

The results are shown in FIG. 2. FIG. 2A is a chromatogram of the IC results after 2.5 minutes. The large rounded peak represents the carbonate ion ($HCO_3^-$), and the curve which starts upward at about the 2.5 minute mark represents the start of the chloride ion ($Cl^-$) peak.

Figure 2B:
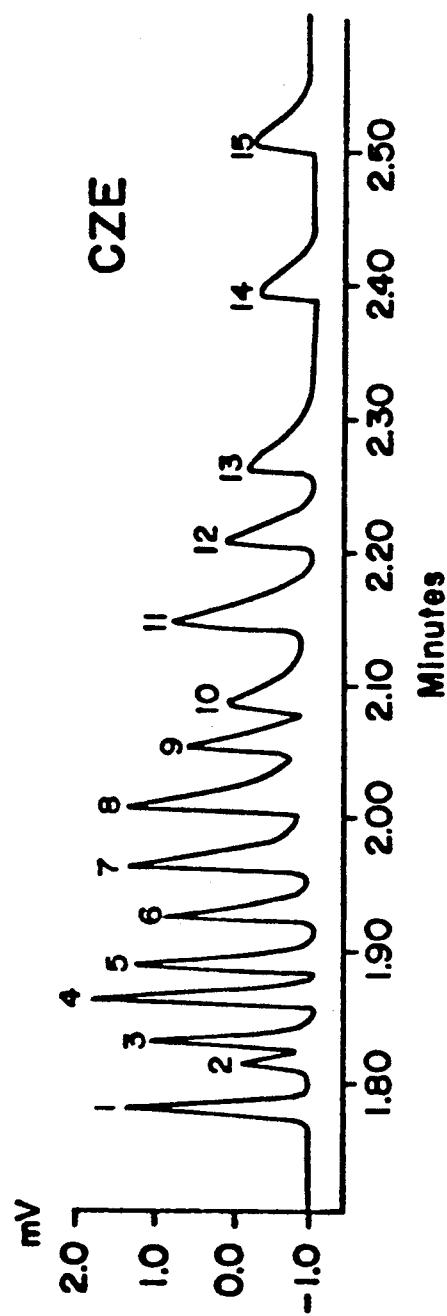

FIG. 2B is a chromatogram showing the CE separation. Separation of all fifteen anions was completed in about 2.5 minutes, and a clear and distinct peak was obtained for each anion.

The results showed that for identical ppm levels of each anion, approximately the same signal to noise ratios were observed by CE from an injection volume of 20 nL as by IC for an injection volume of 100 μl. These results indicate that the CE method is about 5000 times more sensitive than conventional IC. In this example, it took about two minutes for an average IC peak to elute under standard conditions wherein the CE method separated fifteen peaks in the same period of time. The observed increase in sensitivity is due to increased separation efficiency: about 1000 theoretical plates for IC vs. about 100,000 for CZE.

EXAMPLE 5

CE Separation of a Mixture of Nine Anions Using a Modified Capillary

Figure 3:
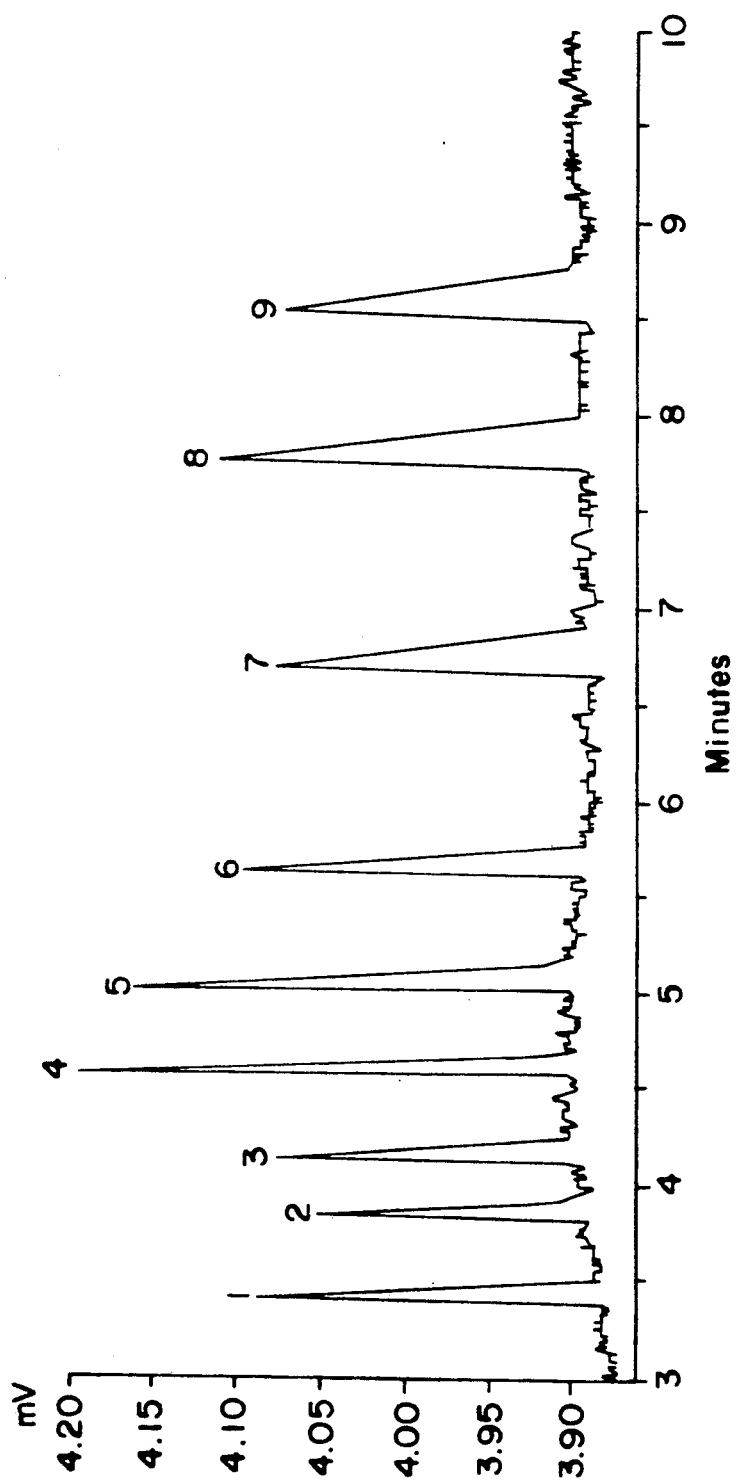
FIG. 3 is a chromatogram showing the separation of nine anions by CE using $Na_2CrO_4$ as the carrier electrolyte and modifying the capillary walls with an uncharged polymer, effectively shielding the silanol groups on the walls.

The separation of a mixture of nine anions was carried out according to the procedure described in Example 1. except that no flow modifier (TTAB) was used. The capillary wall was modified by covering the inner wall with a layer of PSDVB polymer to shield the negative charges of the silanol groups present on the wall. The capillary was 46 cm in length and had an internal diameter of 50 μm. All nine anions were separated by the procedure in less than nine minutes, as shown in FIG. 3. The anions shown in FIG. 3 are:
1. thiosulfate
2. bromide
3. chloride
4. sulfate 5. nitrite
6. nitrate
7. molybdate
8. azide
9. tungstate.

EXAMPLE 6

CE Separation of Five Anions Using an Amphoteric Flow Modifier

Figure 4:
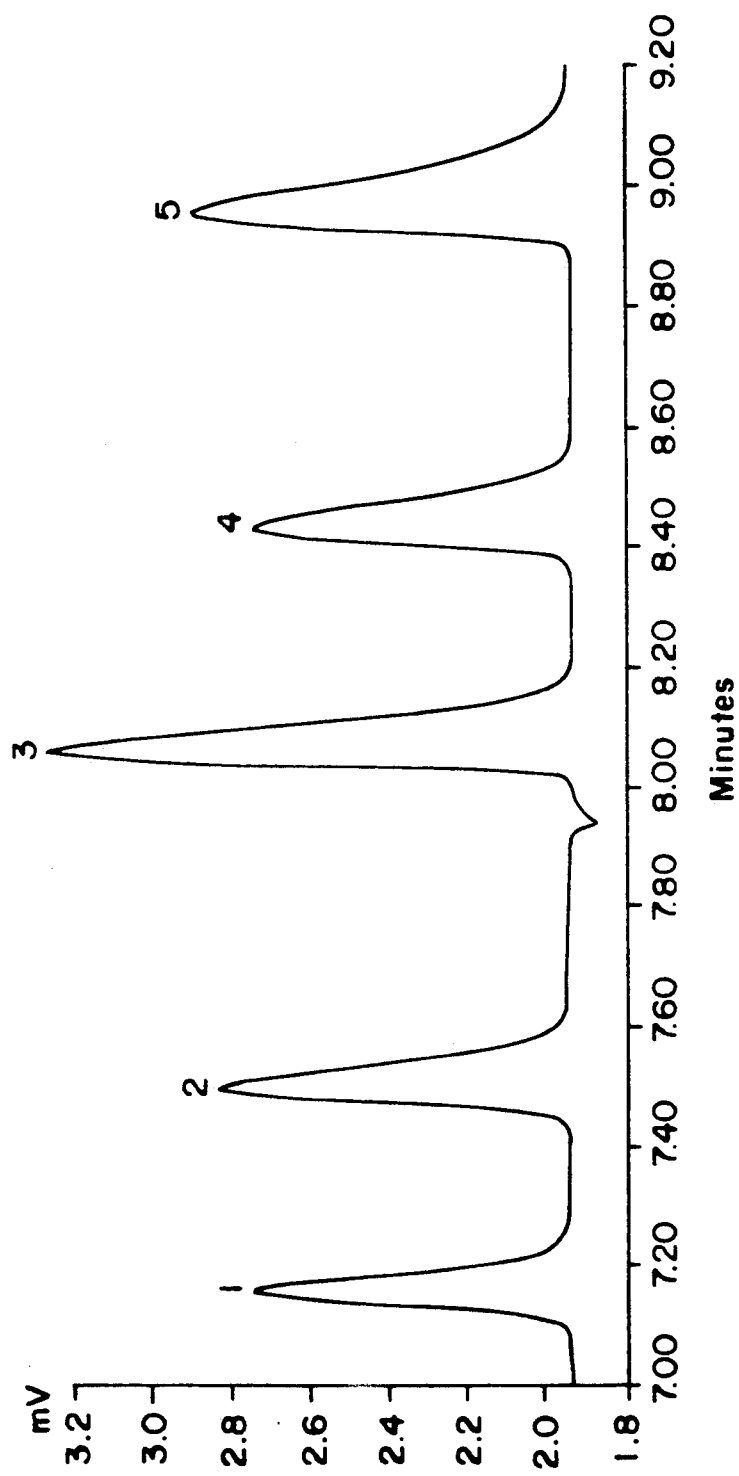
FIG. 4 is a chromatogram showing the separation of five anions by CE using $Na_2CrO_4$ and an amphoteric flow modifier as the carrier electrolyte.

Separation of a mixture of five anions was carried out according to the procedure described in Example 1, except that an amphoteric detergent, 3(N,N-dimethyl-palmitylammonio)propanesulfonate (pH 8, 0.5 mM), was used in lieu of TTAB. The capillary was 60 cm in length and had an internal diameter of 75 μm. All five anions were separated in about nine minutes, as shown in FIG. 4. The anions shown in FIG. 4 are:
1. Br
2. Cl
3. $SO_4$
4. $NO_2$
5. $NO_3$

EXAMPLE 7

Improving Sensitivity of Separation of an Eight Anion Mixture by Electromigrative Sample Introduction CE separation of an eight anion mixture was carried out as described in Example 1 above, except that an electromigration enhancer sodium octanesulfonate, was added to enhance sensitivity for trace amounts of anions.

The carrier electrolyte contained 5 mM chromate and 0.5 mM TTAB electroosmotic flow modifier and was adjusted to pH 8.1. Fused silica capillary (75 μm internal diameter 52 cm from the point of sample introduction to the detector) was used for the separation. During the analysis, the injection side was at −20 kV. The electromigrative sample introduction was carried out at 5 kV for 45 seconds. Sample conductivity was adjusted by the addition of sodium octanesulfonate at 18 μN to the sample. The peak identities, ppb concentrations and nM detection limits (3× the noise), shown in FIG. 5, were as follows: Peak 1:Bromide 4 ppb, 13.6 nM; 2:Chloride 4 ppb, 13 nM; 3:Sulfate 4 ppb, 8.4 nM, 4:Nitrite 4 ppb, 25.4 nM; 5:Nitrate 4 ppb, 24 nM; 6:Fluoride 2 ppb, 19.8 nM and 7-Phosphate 8 ppbm 17.8 nM. The large peak at about 3.2 minutes is the carbonate. The levels of carbonate were not controlled under the conditions of this experiment. These results show that the detection limits (calculated as 3× noise in concentration units) for this separation are in the two nanomolar range, which represents at least a hundredfold increase in sensitivity in comparison with the results achievable in the same carrier electrolyte without the addition of sodium octanesulfonate to the sample.

EXAMPLE 8

Figure 6:
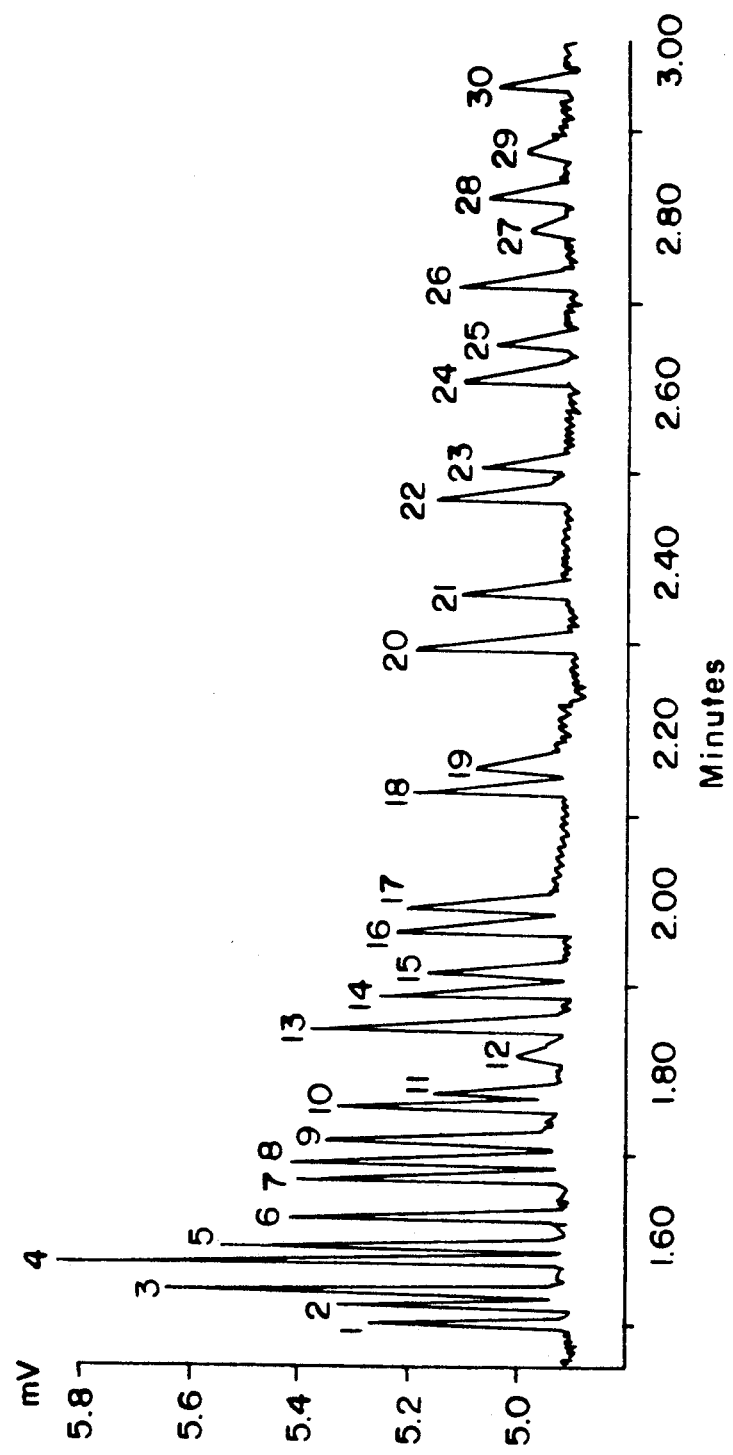
FIG. 6 is a chromatogram showing the separation of thirty anions by CE using TTAB/$Na_2CrO_4$ and electromigrative sample injection.

CE Separation of a Thirty anion Mixture Using Electromigrative Sample Introduction CE separation of a thirty anion mixture was carried out as described in Example 7, using electromigrative sample introduction. The electromigrative sample introduction was carried out at 1 KV for 14 seconds. The capillary was 60 cm in length and had an internal diameter of 50 μm. The electrolyte was 5 mM $Na_2CrO_4$ and 0.5 mM TTAB, pH 8.0. All thirty anions were separated in less than three minutes, as shown in FIG. 6. The anions shown in FIG. 6 are listed below:
1. thiosulfate
2. bromide
3. chloride
4. sulfate
5. nitrite
6. nitrate
7. molybdate
8. azide
9. tungstate
10. monofluorophosphate
11. chlorate
12. citrate
13. fluoride
14. formate
15. phosphate
16. phosphite
17. chlorite
18. galactarate
19. carbonate
20. acetate
21. ethanesulfonate
22. propionate
23. propanesulfonate
24. butyrate
25. butanesulfonate
26. valerate
27. benzoate
28. glutamate
29. pentanesulfonate
30. gluconate

EXAMPLE 9

CE Separation of Nine Anions Using Naphthalene Sulfonic Acid Electrolyte

A mixture of nine anions was separated according to the procedure described in Example 1. The nine anions, designated C4–C10, C12 and C14, are linear alkylsulfonates having from 4 to 14 carbon atoms, at a concentration of 25 ppm each. A capillary 60 cm long and having an internal diameter of 75 μm was used. The electrolyte was 10 mM naphthalene sulfonic acid (30% ACN) adjusted to pH 10 with NaOH. The sample was injected by hydrostatic injection for 30 seconds. Indirect UV detection was used at a wavelength of 254 nm.

Figure 7:
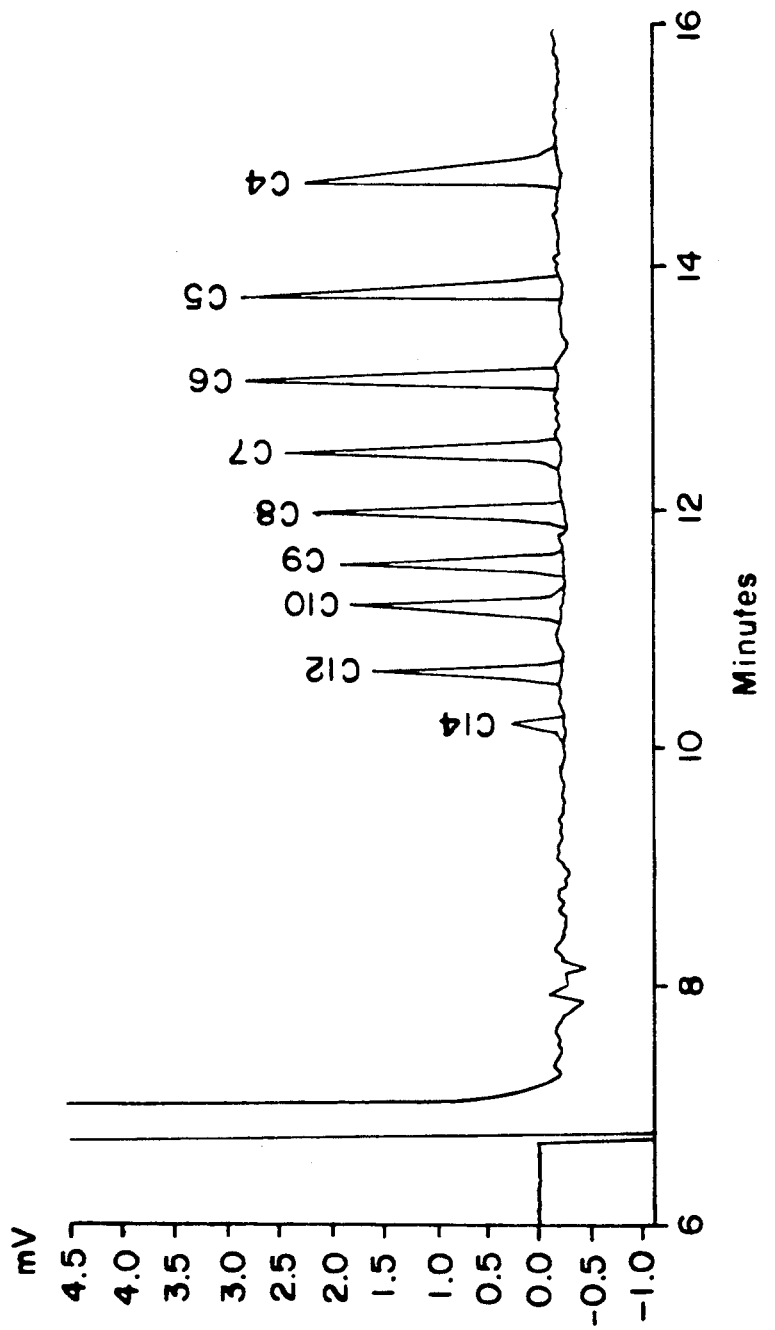
FIG. 7 is a chromatogram showing the separation of nine anions by CE using naphthalene sulfonate as the electrolyte.

The results are shown in FIG. 7. All nine anions were separated and elution was complete in about fifteen minutes.

EXAMPLE 10

General Procedure for CE Separation of Cations Using 4-Methylbenzylamine Electrolyte A sample containing the following seven inorganic cations was prepared: potassium (K), barium (Ba), strontium (Sr), sodium (Na), calcium (Ca), magnesium (Mg) and lithium (Li).

A fused silica capillary externally coated with polyimide was freshly cut from a roll and prepared as described in Example 1. The total capillary length was about 60 cm, and had an internal diameter of 75 μm. The electrolyte was 5 mM 4-methylbenzylamine and 0.021 mM citrate, pH 5.5. The pH was adjusted to pH 5.5 using 2N morpholinoethanesulfonate (MES). A 50 ml beaker and a 100 ml beaker were filled with electrolyte to equal heights. The 50 ml beaker was placed at the anode end of capillary and the 100 ml beaker was placed at the cathode end.

The sample was injected by hydrostatic injection and the separation carried out according to the procedure described in Example 1. The voltage was 25.0 KV Detection was carried out using a UV/Vis CE detector at a wavelength of 214 nm.

Figure 8:
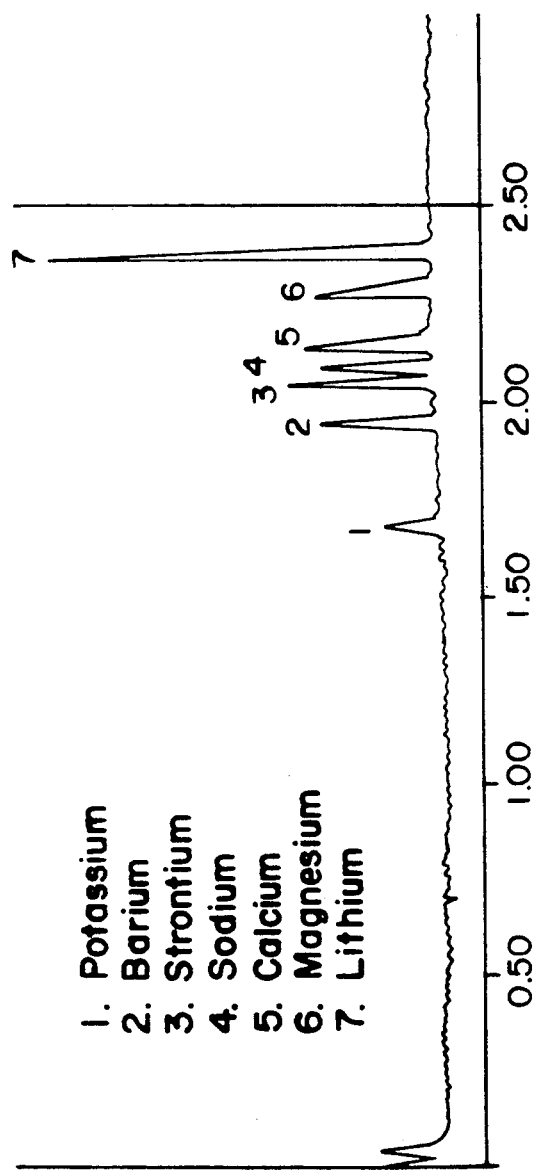
FIG. 8 is a chromatogram showing the separation of seven cations by CE using 4-methylbenzylamine as the carrier electrolyte.

The results are shown in FIG. 8. All seven cations were separated in less than three minutes, and a clear and distinct peak was obtained for each cation. All seven cations were separated within about one minute.

Equivalents

Those skilled in the art will recognize, or be able to ascertain using no more than routine experimentation, equivalents to the specific embodiments of the invention described specifically herein. Such equivalents are intended to be encompassed in the scope of the following claims.

We claim:

1. A method for detecting anions in a sample using capillary zone electrophoresis comprising the steps of:
   a. introducing the sample into a capillary;
   b. immersing the capillary in a carrier electrolyte containing a chromate salt;
   c. applying an electrical current under conditions appropriate for the anions in the sample to move along the capillary toward the anode thereby causing separation of the anions to occur; and
   d. detecting the anions indirectly using a UV/visible photometric detector.

2. The method of claim 1 wherein the chromate salt is sodium chromate having a concentration of from about 1.0 mM to about 20 mM.

3. The method of claim 1 wherein an alkyl quaternary ammonium salt, arsonium salt or phosphonium salt containing at least one alkyl group having more than eight carbon atoms is added to the carrier electrolyte.

4. The method of claim 3 wherein the alkyl quaternary salt is tetradecyltrimethylammonium bromide having a concentration of from about 0.1 mM to about 5.0 mM.

5. The method of claim 3 wherein the alkyl quaternary salt is cetyltrimethyl ammonium bromide having a concentration of from about 0.1 mM to about 5.0 mM.

6. The method of claim 1 wherein the alkyl quaternary ammonium, arsonium or phosphonium salt is immobilized on the capillary wall.

7. The method of claim 1 wherein electrical voltage is from about 5 to about 40 KV.

8. The method of claim 1 wherein an electromigration additive is added to the sample.

9. The method of claim 8 wherein the electromigration additive is selected from the group of: an octanesulfonate salt, a carbonate salt and a citrate salt.

10. The method of claim 9 wherein the electromigration additive is sodium octanesulfonate.

11. The method of claim 1 wherein the anions are complex organic anions selected from the group consisting of: anionic complexes of metals, carboxylic acids, sulfonic acids and alkyl sulfates.

12. The method of claim 1 wherein the anions are inorganic anions.

13. The method of claim 1 wherein a vanadate salt is used in lieu of the chromate salt.

* * * * *